United States Patent [19]
Vidal et al.

[11] Patent Number: 5,785,232
[45] Date of Patent: Jul. 28, 1998

[54] SURGICAL STAPLER

[75] Inventors: Claude Vidal, Santa Barbara; Russell J. Redmond; Alan Plyley, both of Goleta, all of Calif.

[73] Assignee: VIR Engineering, Santa Barbara, Calif.

[21] Appl. No.: 633,668

[22] Filed: Apr. 17, 1996

[51] Int. Cl.$^6$ ............................................. A61B 17/068
[52] U.S. Cl. ..................... 227/176.1; 227/19; 227/180.1
[58] Field of Search ............................ 227/19, 175.3, 227/180.1, 181.1, 176.1

[56] References Cited

U.S. PATENT DOCUMENTS

| | | | |
|---|---|---|---|
| 4,892,244 | 1/1990 | Fox et al. | 8/19 |
| 5,106,008 | 4/1992 | Tompkins et al. | 178/8 |
| 5,253,793 | 10/1993 | Green et al. | 178/176 |
| 5,332,142 | 7/1994 | Robinson et al. | 178/19 |
| 5,382,254 | 1/1995 | McGarry et al. | 143/142 |
| 5,397,046 | 3/1995 | Savage et al. | 176/179 |
| 5,413,267 | 5/1995 | Solyntjes et al. | 176/19 |
| 5,413,268 | 5/1995 | Green et al. | 176/178 |

FOREIGN PATENT DOCUMENTS

| | | | |
|---|---|---|---|
| 0373762 | 11/1989 | European Pat. Off. | A61B 17/10 |
| 0488768 | 11/1991 | European Pat. Off. | A61B 17/072 |
| 0489436 | 12/1991 | European Pat. Off. | A61B 17/072 |
| 9210976 | 7/1992 | European Pat. Off. | A61B 17/10 |
| 0537572 | 10/1992 | European Pat. Off. | A61B 17/00 |
| 9424943 | 11/1994 | WIPO | A61B 17/072 |

*Primary Examiner*—Scott A. Smith
*Attorney, Agent, or Firm*—James E. Brunton

[57] ABSTRACT

An improved surgical stapler having first and second pivotally interconnected structural members each including a handle portion and a jaw portion. The structural members are pivotally movable between a closed position wherein their jaw portions are in a closely spaced relationship to an open position wherein their jaw portions are spaced apart a substantial distance. A locking member is pivotally connected to one of the structural members for pivotal movement between a first position wherein the locking member is generally aligned with the structural member and a second position wherein the free end of the locking member is spaced apart from the outboard end of the structural member. When actuated, the locking member functions to forcefully move the structural members toward a closed position so that the tissue to be stapled can be securely clamped between the jaw portions of the instrument. A staple cartridge of novel design is removably connected to one of the first and second structural members and contains a plurality of staples for stapling together tissue disposed between the jaw portions of the instrument. A novel jaw stabilizing element is provided either on the staple cartridge or on the disposable anvil of the device for insuring proper spacing between the handle portions of the instrument and in this way functions to maintain optimum jaw closure for every tissue thickness by restricting the undesirable bending of the handle portions as the tissue to be stapled is compressed between the jaw portions.

4 Claims, 7 Drawing Sheets

SURGICAL STAPLER

BACKGROUND OF THE INVENTION

1. Field of the Invention

The present invention relates generally to surgical stapling devices and to the staple cartridges used therewith. More particularly, the invention concerns an improved surgical stapling apparatus which includes a staple cartridge that embodies a novel jaw stabilizer which restricts the undesirable bending of the handle portions of the stapler toward each other in response to separating forces exerted on the cooperating jaw portions as the tissue to be stapled together is compressed between the jaw portions.

2. Discussion of the Invention

Surgical staplers are frequently used in surgical procedures for suturing body tissue as, for example, intestinal and gastric walls. A well known type of prior art surgical stapling apparatus is currently available from the Minnesota, Mining and Manufacturing Company of St. Paul, Minn. under the trade designation "The ILA Stapler", catalog #3957. This apparatus is exemplary of the so-called linear stapler, which is a device that enables the surgeon to place one to several rows of surgical staples in body tissue or organs. By way of example, a typical procedure in which the linear stapler may be used is a pneumectomy, that is a removal of a portion of a patient's lungs. During this procedure, the linear stapler may be used several times. In the process, several arteries are simultaneously severed by the cutting means provided on the linear stapler and sealed by the formed staples.

One of the major drawbacks of the prior art linear staplers is the failure of the jaws of the stapler to clamp the tissue in such a way that the tissue is adequately compressed to permit proper staple formation. Because the tissue is basically water, there can be some significant bending of the stapler jaws as the tissue is compressed. Although increasing the size of the cantilever beam would appear to be the logical solution to the bending problem, there is a substantial clinical penalty to pay for this solution because the increased size of the beam makes it very difficult for the surgeon to place the instrument into the locations where these staplers are most commonly needed, as, for example, into the lumen of the small intestine, or in the deep pelvis at the distal section of the colon.

With respect to the previously mentioned ILA Stapler, this widely used prior art device comprises first and second pivotally interconnected, elongated structural members each having a handle portion and a jaw portion. A staple carrying cartridge of conventional design is removably mounted on one of the jaw portions. In the ILA Stapler, the structural members are pivotally movable between a closed position, wherein the jaw portions are in closely spaced relationship, and an open position wherein the jaw portions are further spaced apart. An elongated locking member is pivotally connected to the second structural member and operably engages the first structural member in a manner to forcefully move the structural members into their closed position so that high compressive forces can be applied on tissues to be stapled. The staple carrying cartridge of the ILA apparatus includes manually actuatable means for sequentially ejecting the staples from the cartridge in a manner to staple together the tissues disposed between the jaw portions of the instrument.

Typically, the lengths of the rows of staples applied by prior art stapling instruments have been limited in length to about 50 millimeters (2 inches). This is because compression of tissues between jaw portions of sufficient length to apply longer rows would cause the jaw portions to deflect excessively away from each other and result in improper spacing between the staple forming anvil of the instrument and the cartridge, particularly near the distal ends of the jaw portions. This, in turn, causes incomplete closure of the staples resulting in poor hemostasis in the tissues being stapled.

One solution to the aforementioned problem is described in U.S. Pat. No. 4,429,695 wherein it is suggested that supports be provided at opposite ends of a knife that cuts between the rows of staples. These supports are moved along the jaw portions with the knife so as to hold the anvil and cartridge in the proper spaced relationship as the staples are ejected and closed. The use of such supports, however, requires that the jaw portions be of sufficiently large cross sectional area to receive the supports. Further, moving such supports along the jaw portions increases the force needed to operate the stapling instrument, particularly when stapling tissue that is highly compressed. Additionally, the solution is available only where a knife is used to cut tissue between the rows of staples, which cutting is not necessary or desirable in all instances.

Another solution to the problem is described in U.S. Pat. No. 4,633,874 wherein it is suggested that urging the jaw members apart at a position remote from the latching mechanism through the action of a cam mechanism actuated by the forward motion of the pusher-knife subassembly will resist the forces extended on the anvil and staple carrying portions of the jaw members and therefore help control formed staples height. This instrument structure, however, still allows the jaw members to flex between their pivot point and their proximal end, where this additional force is provided by the mechanism described in that invention. As a result, it does not fully fulfill its intended purpose.

Still another solution to the problem is proposed in U.S. Pat. No. 4,863,088 (the '088 patent) issued to one of the present inventors. The solution proposed in this latter patent does not require the movement of supports along the jaw portions and advantageously allows the instrument to be used with or without a knife for cutting between applied row of staples. As pointed out in the '088 patent, a structural analysis of the ILA Stapler shows that the undesired deflection of the jaws results primarily because the handle parts of the structural members in their closed position define a space between the structural members over the majority of the distance between the first and second ends of the handle parts. This space allows the handle parts to bend so that their centers deflect toward each other while the jaw parts effectively pivot around the surfaces of the structural members in engagement with each other at the first ends of the handle parts, resulting in separation between the jaw parts increasing toward their distal ends. This problem of the undue deflection is proposed to be solved in the '088 patent by providing a protuberance on the handle part of one of the structural elements, which protuberance contacts the handle part of the opposing structural element when the structural elements are in the closed position. This protuberance is strategically constructed and arranged so as to effectively restrict bending and deflection of the handle portions of the device toward each other in response to separating forces applied to the jaw portions by the tissue being compressed therebetween. This proposed solution advantageously permits scale up of the instrument to one that will deliver at least 100 millimeter long rows of staples. Because of the pertinence of U.S. Pat. No. 4,863,088, this patent is hereby incorporated by reference as through fully set forth herein.

While the apparatus described in the '088 patent constitutes a substantial advance in the art, it has exhibited certain shortcomings in actual use. More particularly, the provision of a protuberance on one of the handle portions of the device which, in fact, effectively minimizes jaw deflection requires that the structural members of the instrument be manufactured to extremely close tolerances. Additionally, experience has shown that each time the stapler is used, the metal to metal contact in this high stress area produces a flattening or "coining" of the critical contact surfaces. This coining effect changes the position of contact between these surfaces, which causes a reduced preload to the jaws and results in more deflection of the stapler s jaws and correspondingly a more open staple formation. In practice, such an increase in open staple formation over time can undesirably result in excessive bleeding and a weaker staple line.

As will be better understood from the disclosure which follows, the apparatus of the present invention elegantly solves many of the problems exhibited by the prior art linear stapling devices, including the improved ILA Stapler, by providing either a rigid or predictably "crushable" jaw stabilizing element at the proximal end of the disposable staple cartridge itself. Since a fresh staple cartridge is inserted into the apparatus after each stapling procedure, it follows that a new jaw stabilizing element is provided each time the apparatus is used. The novel jaw stabilizing element, which is formed on the staple cartridge, insures proper spacing between the handle portions and functions to maintain optimum jaw closure for every tissue thickness.

SUMMARY OF THE INVENTION

By way of summary, the surgical stapler of the present invention, is of the character having first and second pivotally interconnected structural members each including a handle portion and a jaw portion. The structural members are pivotally movable between a closed position wherein their jaw portions are in a closely spaced relationship to an open position wherein their jaw portions are spaced apart a substantial distance. A locking member is pivotally connected to one of the structural members for pivotal movement between a first position wherein the locking member is generally aligned with the structural member and a second position wherein the free end of the locking member is spaced apart from the outboard end of the structural member. When actuated, the locking member functions to forcefully move the structural members toward a closed position so that the tissue to be stapled can be securely clamped between the jaw portions of the instrument. A staple cartridge of novel design is removably connected to one of the first and second structural members and contains a plurality of staples for stapling together tissue disposed between the jaw portions of the instrument as they are moved into the closed position. An extremely important feature of the apparatus of the invention is the provision, as a part of either the staple cartridge, or the removable anvil, of jaw stabilizer means for restricting bending of the handle portions of the structural members as the tissue is clamped between the jaw portions. The jaw stabilizer means is so constructed and arranged as to insure proper spacing between the handle portions of the instrument and to maintain optimum jaw closure for every tissue thickness. Since the staple cartridge and the anvil are replaced after each stapling procedure, a fresh jaw stabilizer means is presented each time the instrument is used.

With the foregoing summary description in mind, it is an object of the invention to provide, as a part of the staple cartridge of the instrument, novel stabilizer means for insuring proper spacing between the handle portions of the instrument and thereby effectively restricting undue bending of the handle portions of the structural members as they move toward the closed, tissue clamping position. In this way, proper staple formation is insured and undesirable bleeding along the staple line is either eliminated or substantially minimized.

Another object of the invention is to provide a surgical stapler of the aforementioned character, in which the stabilizer means, being a part of either the removable staple cartridge, or the removable anvil, is automatically replaced each time the device is used.

Another object of the invention is to provide a surgical stapler as described in the preceding paragraph in which, in one embodiment of the invention, the stabilizer means comprises a metal insert that is press fit into a plastic sleeve-like body provided on a replaceable staple cartridge.

Another object of the invention is to provide a surgical stapler as described in the foregoing paragraphs in which the stablizer means comprises a metalic element connected to a spring like extension provided on the replaceable, disposable anvil.

Another object of the invention is to provide a surgical stapler of the character described in which the stabilizer means comprises a crushable insert which is carried either by the staple cartridge, or the removable anvil, and which is crushed to a predetermined thickness when the instrument is fully closed.

Another object of the invention is to provide an apparatus of the character described in the preceding paragraph in which the stabilizer means of the invention can be easily and inexpensively implemented into either a staple cartridge or a novel anvil assembly that is readily usable with several types of prior art linear staplers.

Another object of the invention is to provide a staple containing cartridge for use with prior art surgical staplers that includes jaw stabilizer means of simple design and one which is easy to use and inexpensive to manufacture.

Another object of the invention is to provide a removable anvil for use with prior art surgical staplers that includes jaw stablizer means of simple and inexpensive design.

DESCRIPTION OF THE INVENTION

Figure 1:
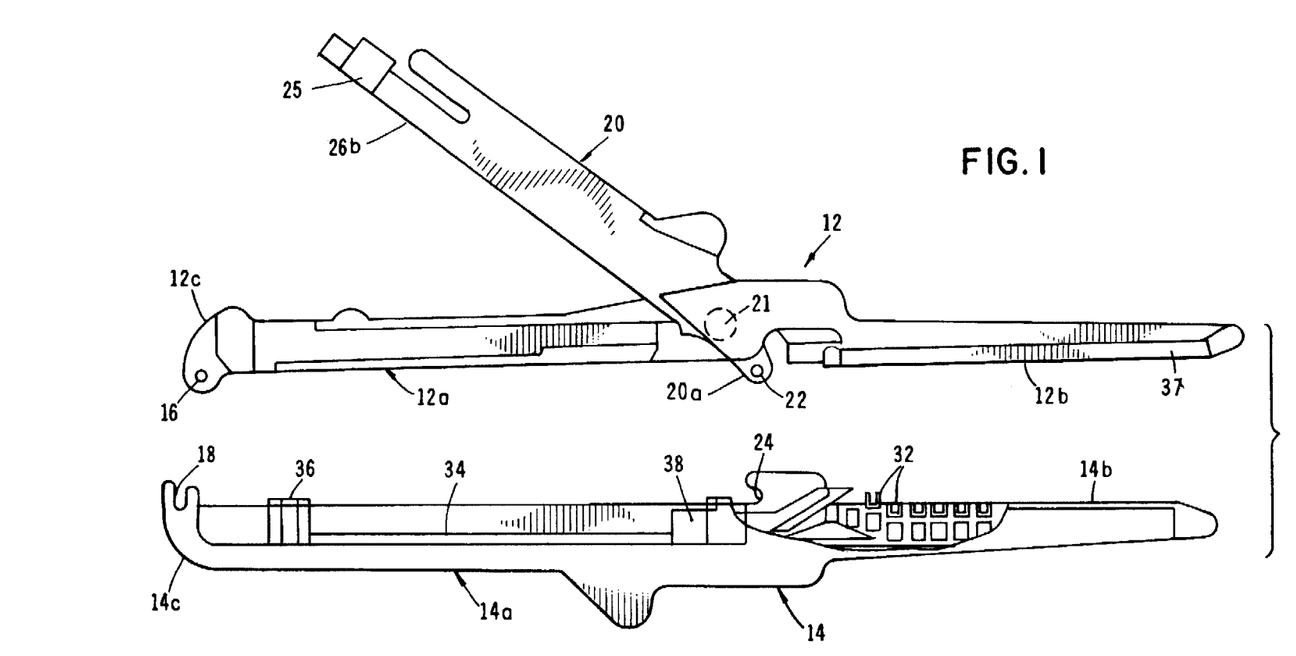
FIG. 1 is a side-elevational, exploded view of the improved surgical stapler of one form of the invention.
Figure 2:
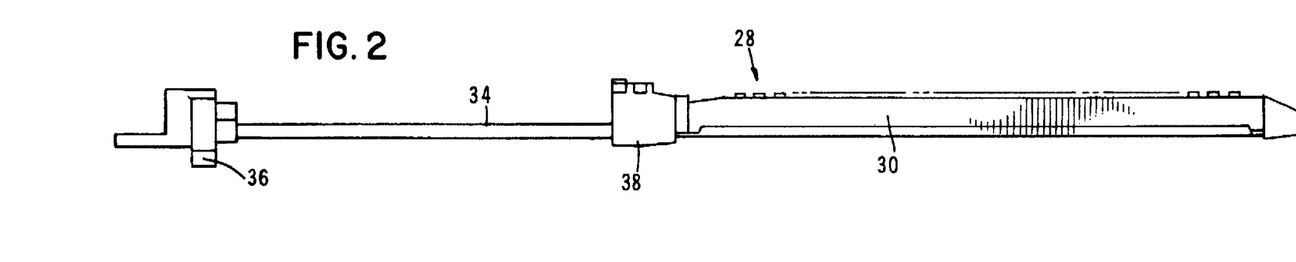
FIG. 2 is a side-elevational view of one form of the staple cartridge of the invention which is usable in the apparatus shown in FIG. 1.
Figure 3:
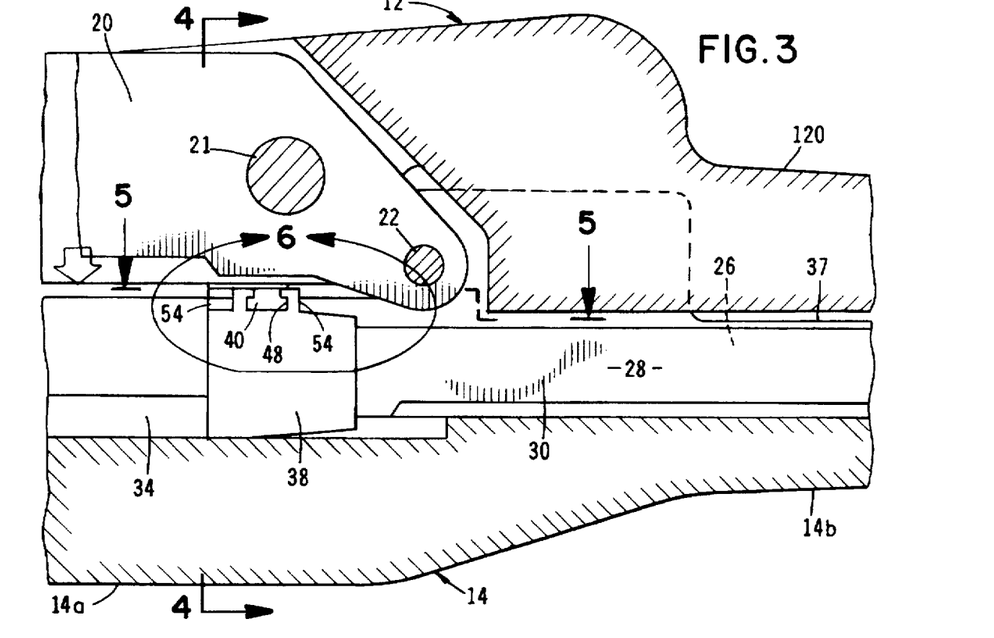
FIG. 3 is a greatly enlarged, side-elevational view of the central portion of the surgical stapling apparatus showing the staple cartridge mounted between the first and second structural members of the stapling instrument.

Referring to the drawings and particularly to FIGS. 1, 2, and 3, one form of the surgical stapler of the present invention can be seen to comprise first and second elongated structural members 12 and 14, each having a handle portion designated as portions 12a and 14a respectively and a jaw portion designated here as portions 12b and 14b respectively. Structural members 12 and 14 are pivotally interconnected by first pivot means located proximate the second ends 12c and 14c respectively of the structural members. These first pivot means, which here comprise a transversely extending pivot pin 16 provided on member 12 and a cooperating pin receiving slot 18 provided on member 14, permit pivotal movement of the structural members between the closed position shown in FIG. 3, wherein the jaw portions 12b and 14b are in a closely spaced relationship, to an open position wherein the jaw portions are spaced further apart.

Also forming a part of the surgical stapler of this first embodiment of the invention is a locking member 20 having first and second ends 20a and 20b. Locking member 20 is pivotally connected to first structural member 14 by a second pivot means located intermediate the ends of the structural member. Locking member 20 is pivotally movable relative to first structural member 12 about the second pivot means between a first position, shown in FIG. 3, wherein the locking member is generally aligned with first structural member 12 and a second position, shown in FIG. 1, wherein the second end 20b of the locking member is spaced apart from the end 12c of structural member 12. The second pivot means here comprises a transversely extending pivot pin 21 which interconnects locking member 20 with first structural member 12 in the manner best seen in FIGS. 1 and 3.

Locking member 20 is also provided with a transversely extending engagement pin 22 which is receivable within a pin engagement slot 24 provided in structural member 14 (FIG. 1). When structural members 12 and 14 are pivotally interconnected in the manner shown in FIG. 3 and, when engagement pin 22 is disposed within slot 24, movement of the locking member from the second position shown in FIG. 1 into the first position shown in FIG. 3 causes the first and second structural members to move into the closed position shown in FIG. 3. Means for releasable engagement between the locking member and structural member 12 are provided in the form of a locking assembly 25 of the character described in the '088 patent.

Figure 4:
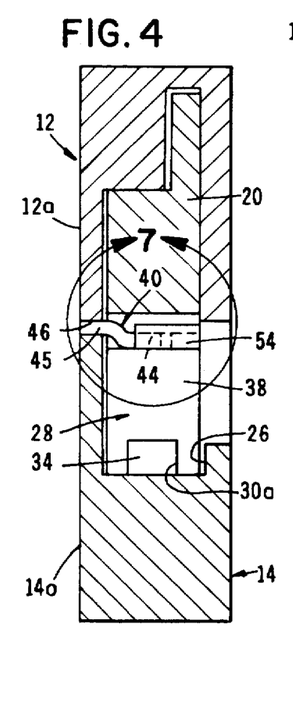
FIG. 4 is a cross-sectional view taken along lines 4—4 of FIG. 3.
Figure 5:
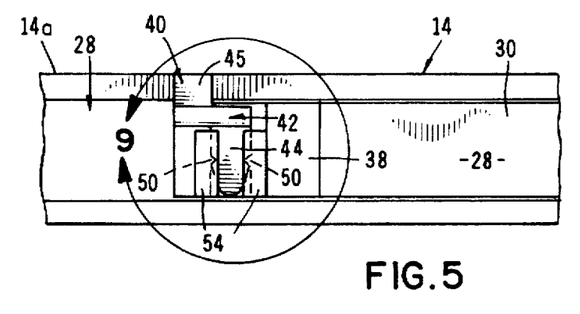
FIG. 5 is a view taken along lines 5—5 of FIG. 3.
Figure 6:
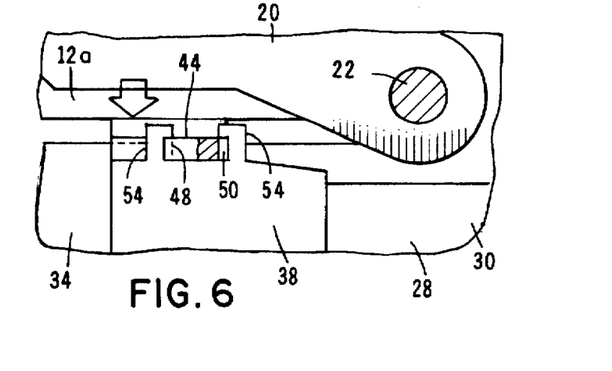
FIG. 6 is an enlarged, fragmentary view of the portion designated as 6 in FIG. 3.

As best seen by referring to FIG. 4, structural member 14a is provided with a longitudinally extending channel 26 which closely receives the staple cartridge assembly 28 of the invention. Staple cartridge assembly 28 forms a part of the stapling means of the invention and comprises a staple carrying body portion 30 for carrying a plurality of surgical staplers 32 (FIG. 2) and a staple camming means for sequentially ejecting the staples from the body portion of the staple cartridge assembly. Staple carrying body portion 30 includes an elongated slideway 30a (FIG. 4) which slidably receives the staple camming means, here provided in the form of an elongated drive rod 34 having at its outboard end a finger engaging tab or pusher member 36. With this construction drive rod 34 can be pushed longitudinally of slideway 30a by forces exerted on member 36. This forward movement of the drive rod causes sequential ejection of the staples 32 from the cartridge body 30 and, in a manner presently to be described, forces the staples into tissue disposed between jaw portions 12b and 14b of the structural members and into forming engagement with an anvil 37 provided on structural member 12. Provided proximate one end of body portion 30 and located approximately at the center of the staple cartridge assembly as shown in FIG. 2 is a central sleeve-like portion 38 which is suitably interconnected with body portion 30 of the staple cartridge assembly.

Figure 7:
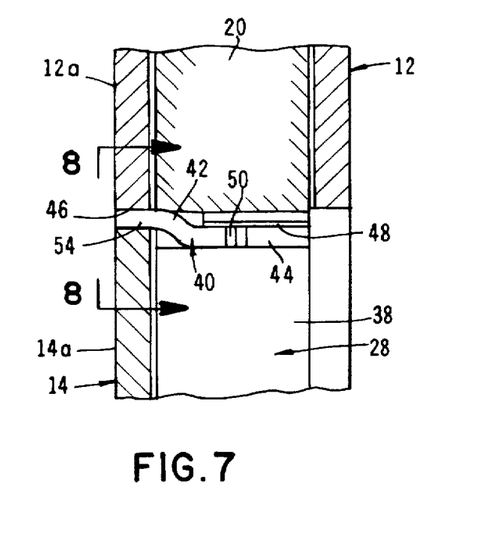
FIG. 7 is an enlarged, fragmentary, cross-sectional view of the portion designated as 7 in FIG. 4.
Figure 8:
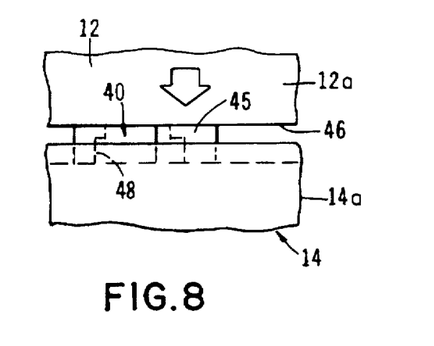
FIG. 8 is a view taken along lines 8—8 of FIG. 7.
Figure 9:
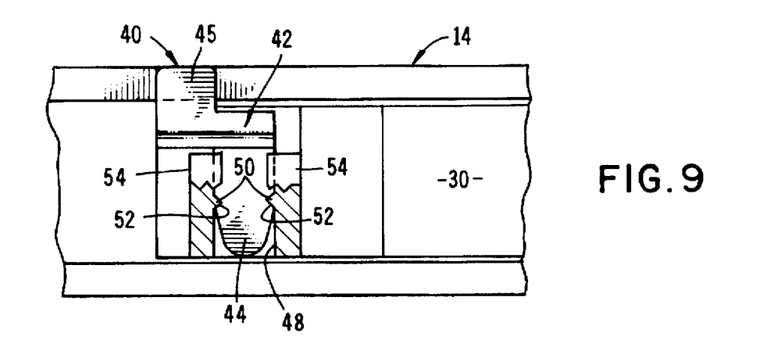
FIG. 9 is an enlarged, fragmentary view of the area designated as 9 in FIG. 5.
Figure 10:
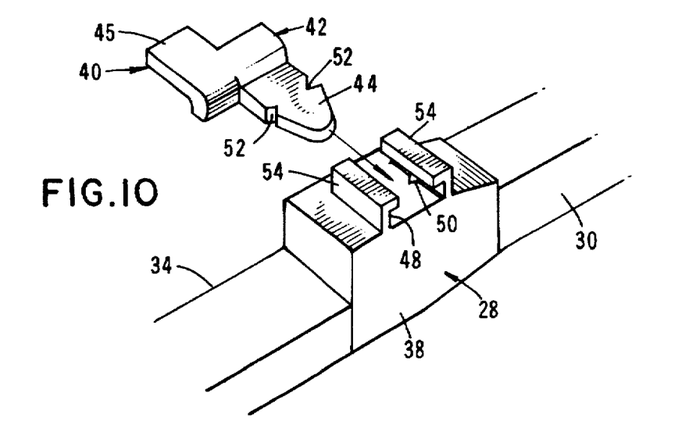
FIG. 10 is a fragmentary, generally perspective view illustrating the manner of attachment of one form of the novel jaw stabilizer member of the invention to the staple containing cartridge.

An extremely important aspect of the surgical stapler of the present invention resides in the provision of jaw stabilizer means for restricting bending of the handle portions of the structural members as the tissue disposed between the jaw portions thereof is compressed as a result of the structural members moving toward the closed position shown in FIG. 3. One form of this novel jaw stabilizing means is illustrated in FIGS. 3 through 10 and, as there shown, comprises a stabilizing member 40 which is connected to the replaceable staple cartridge assembly 28 (FIG. 10). The stabilizer member of this form of the invention comprises a central body portion 42 from which a connecting tab or tongue 44 extends in one direction. Extending from body portion 42 in the opposite direction is a spacer segment 45, which segment extends between handle portions 12a and 14a of the structural members and into the space 46 which is defined thereby when the handle portions are in their closed position (FIGS. 4 and 7).

Referring to FIG. 10, it can be seen that sleeve-like portion 38 of the staple cartridge assembly is provided with a transversely extending groove 48 into which connecting tab 44 is closely received. In the present form of the invention, groove 48 includes a pair of inwardly extending, oppositely disposed, generally angularly shaped retaining protuberances 50 which are lockably receivable within mating, generally angularly shaped indentations 52 provided in connector tab 44. With this construction, when connecting tab 44 is inserted into groove 48, locking protuberances 50 will be lockably received within locking indentations 52 so as to lock the stabilizer member securely in position relative to portion 38 of the staple cartridge assembly. In this embodiment of the invention, stabilizer member 40 is preferably constructed of a rigid, nondeformable material such as steel, ceramic or the like. Body portion 38 of the staple cartridge assembly, on the other hand, is preferably constructed from a moldable plastic material and includes upstanding "ALIT" shaped side walls 54 which define groove 48. Walls 54 are preferably yieldably deformable to permit insertion and locking of connector tab 44 of stabilizer member 40.

With the novel construction described in the preceding paragraph, as structural members 12 and 14 are moved into the closed position shown in FIGS. 3 and 4, spacer element 45 will be engaged by the opposing surfaces of the handle portions 12a and 14a respectively in a manner to restrict bending of the handle portions of the structural members as the tissue disposed between the jaw portions of the structural members is compressed as a result of the members being moved toward their closed position by actuation of locking member 20. Spacer element 45 is of a precisely determined thickness that effectively restricts bending and deflection of the handle portions 12a and 14a of the instrument in response to separating forces applied to the jaw portions by the tissue being compressed therebetween. As previously mentioned, since a new staple cartridge assembly is provided after each stapling operation, a new stabilizer means is also presented each time the instrument is used for the stapling procedure. This elegantly solves the problem inherent in devices of the character described in the '088 patent since, even if some slight deformation to spacer element 45 occurs during the stapling operation, a fresh spacer element is provided for the next ensuing stapling operation.

Figure 11:
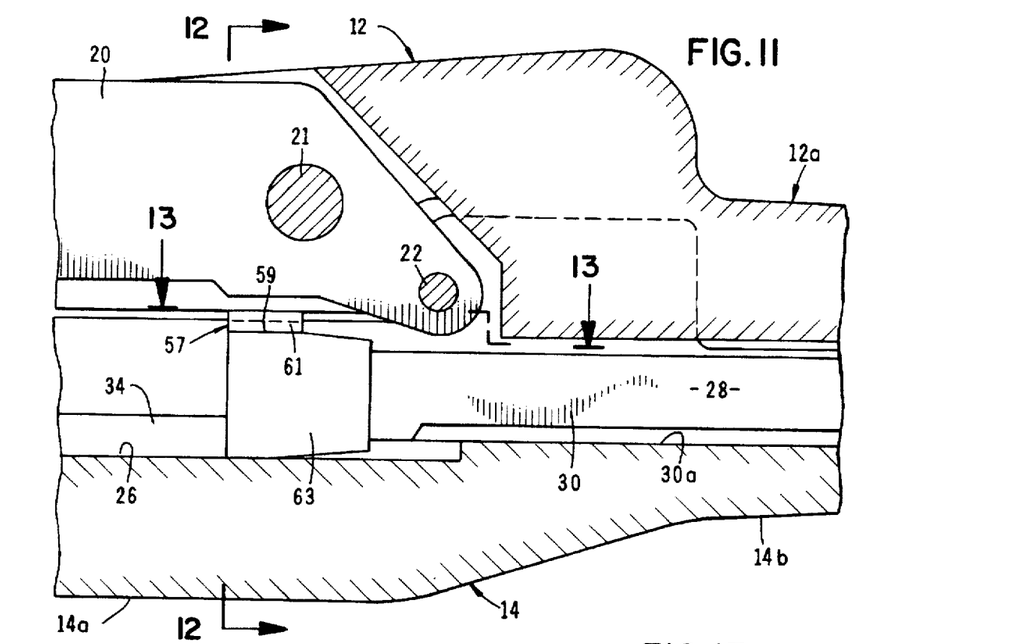
FIG. 11 is an enlarged, fragmentary, side-elevational view similar to FIG. 3, but showing another form of staple cartridge assembly disposed between the first and second structural members of the surgical instrument.
Figures 12, 13, 14:
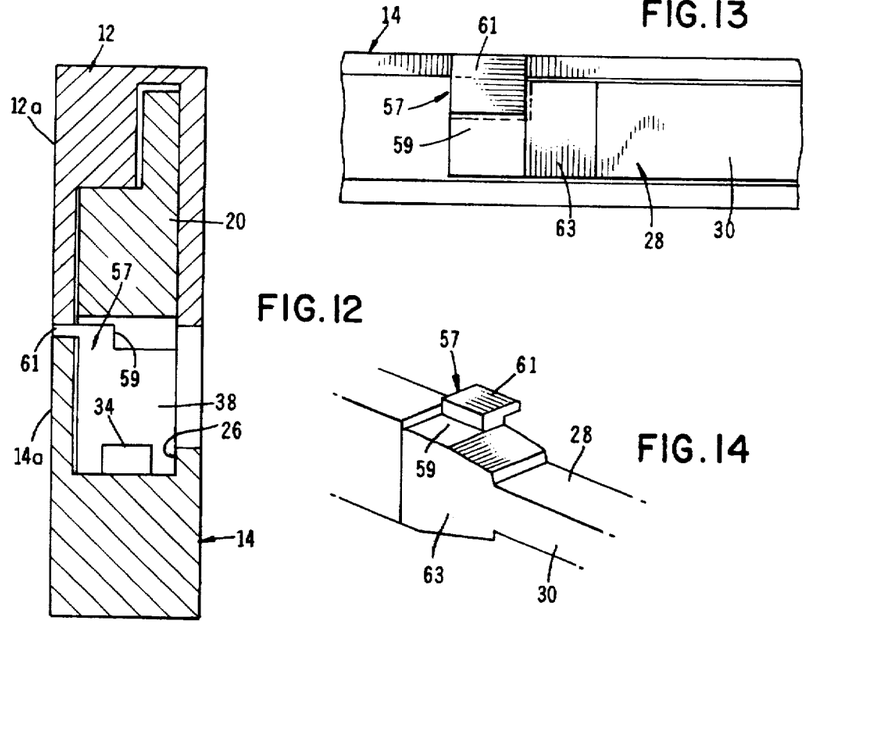
FIG. 12 is a view taken along lines 12—12 of FIG. 11
FIG. 13 is a view taken along lines 13—13 of FIG. 11.
FIG. 14 is a generally perspective, fragmentary view of the central portion of the staple containing cartridge assembly of this latest form of the invention illustrating the construction of the jaw stabilizing member of the assembly.

An alternate form of jaw stabilizing means of the invention is illustrated in FIGS. 11 through 14. This alternate form of stabilizing means is somewhat similar to that shown in FIGS. 3 through 10, but uniquely comprises a stabilizing member 57, a portion of which is controllably crushable. As before, the stabilizing member is connected to the replaceable staple cartridge assembly 28 and includes a central body portion 59 from which a spacer segment 61 extends (FIG. 12). As before, segment 61 extends between handle portions 12a and 14a of the structural members, but unlike segment 45 is controllably crushable rather than being constructed from a rigid material.

Referring to FIG. 14, it can be seen that stabilizer member 57 is integrally formed with a sleeve-like portion 63 of the staple cartridge assembly and is generally "L" shaped in section.

Sleeve-like portion 63 and stabilizer member 57 are preferably molded in a single piece from a suitable type of moldable plastic having physical characteristics such that portion 61 of the stabilizer member will be controllably crushed to a predetermined extent as the structural members 12 and 14 move into their closed position due to actuation of locking member 20. Materials suitable for forming portion 61 of the stabilizer means include ABS, polycarbonate, or nylon (in their natural or glass reinforced condition) as well as a number of other moldable plastics well known to those skilled in the art.

With the novel construction described in the preceding paragraph, as structural members 12 and 14 are moved into the closed position show n in FIGS. 11 and 12, crushable spacer segment 61 will be engaged by the inboard surfaces of the handle portions 12a and 14a respectively and will be crushed to a predetermined thickness which is optimum for restricting bending of the handle portions of the structural members as the tissue disposed between the jaw portions of the structural members is compressed as a result of the members being moved toward their closed position by actuation of locking member 20. Once again, since a new staple cartridge assembly is provided after each stapling operation, a new stabilizer means is presented each time the instrument is used for the stapling procedure.

Still another form of the surgical stapler of the present invention is shown in FIGS. 15 through 18. This form of the surgical stapler is similar in many respects to that shown in FIGS. 1 through 10 and like numbers are used to identify like components. The major difference between this latest embodiment and that shown in FIGS. 1 through 10 resides in the fact that the jaw stabilizer means is carried by a removable, disposable anvil rather than by the staple cartridge.

As before, the instrument comprises first and second elongated structural members 12 and 14, each having a handle portion designated as portions 12a and 14a respectively and a jaw portion designated here as portions 12b and 14b respectively. Structural members 12 and 14 are pivotally interconnected by first pivot means of the character previously described. These first pivot means, permit pivotal movement of the structural members between the closed position shown in FIG. 16, wherein the jaw portions 12b and 14b are in a closely spaced relationship, to an open position wherein the jaw portions are spaced further apart.

Figure 16:
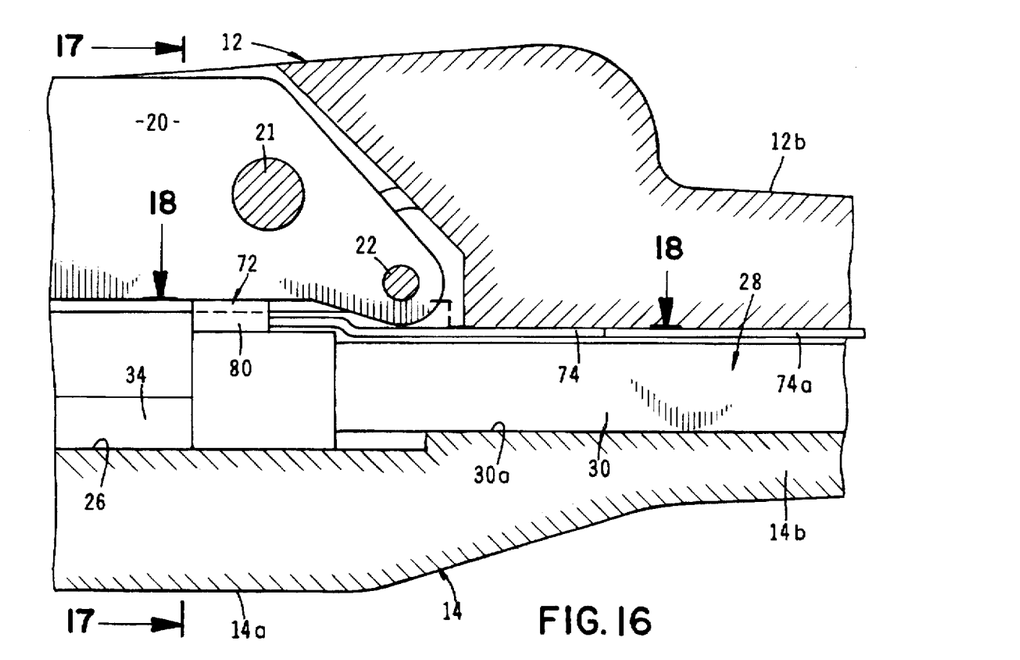
FIG. 16 is a greatly enlarged, side-elevational view of the central portion of the alternate form of surgical stapling apparatus showing the first and second structural members of the stapling instrument in a closed configuration.
Figure 17:
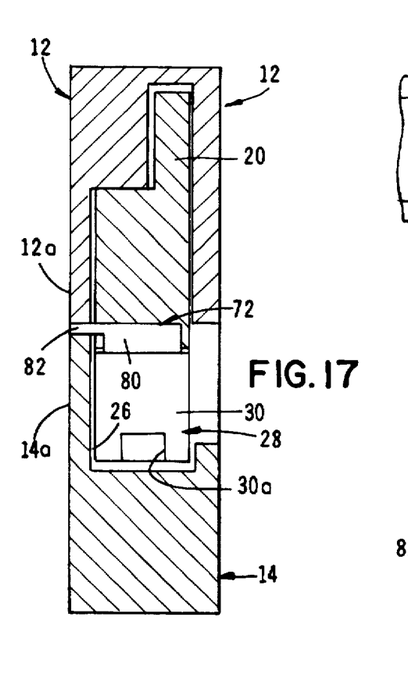
FIG. 17 is a cross-sectional view taken along lines 17—17 of FIG. 16.

Also forming a part of the surgical stapler of this latest embodiment of the invention is a locking member 20 having first and second ends 20a and 20b. Locking member 20 is of the character previously described and is pivotally connected to first structural member 14 by a second pivot means which is located intermediate the ends of the structural member. Locking member 20 is pivotally movable relative to first structural member 12 about the second pivot means between a first position, wherein the locking member is generally aligned with first structural member 12 and a second position, wherein the second end 20b of the locking member is spaced apart from the end 12c of structural member 12.

Figure 15:
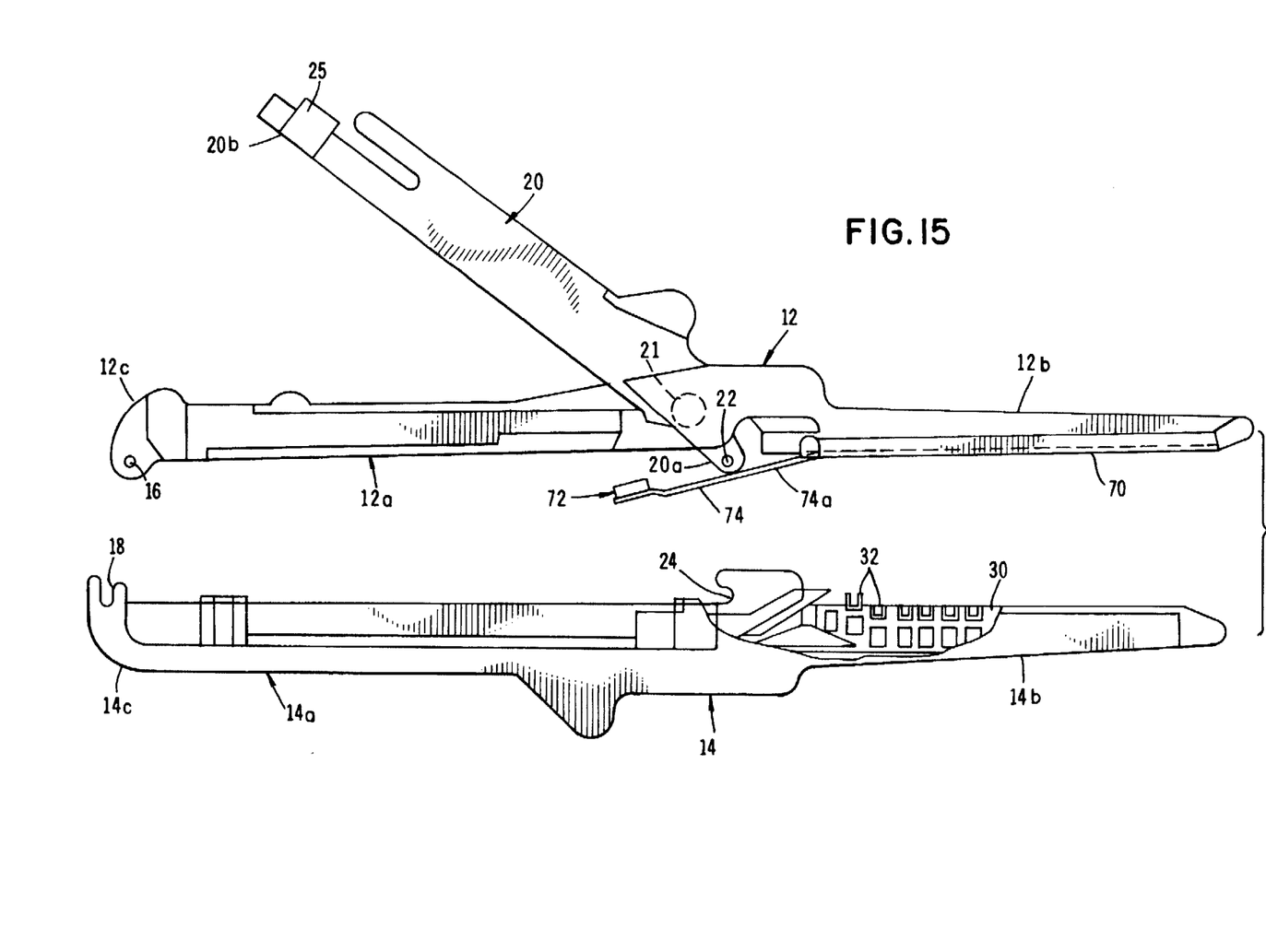
FIG. 15 is a side-elevational, exploded view of an alternate form of the improved surgical stapler of the invention.

Locking member 20 is also provided with a transversely extending engagement pin 22 which is receivable within a pin engagement slot 24 provided in structural member 14 (FIG. 15). When structural members 12 and 14 are pivotally interconnected in the manner shown in FIG. 16 and, when engagement pin 22 is disposed within slot 24, movement of the locking member from the second position into the first position causes the first and second structural members to move into the closed position shown in FIG. 16. Means for releasable engagement between the locking member and structural member 12 are provided in the form of a locking assembly 25 of the character described in the '088 patent.

As in the earlier described embodiments, structural member 14a is provided with a longitudinally extending channel 26 which closely receives the staple cartridge assembly 28 of the invention which comprises a staple carrying body portion 30 for carrying a plurality of surgical staplers 32 and a staple camming means for sequentially ejecting the staples from the body portion of the staple cartridge assembly. Staple carrying body portion 13 includes an elongated slideway 30a (FIG. 17) which slidably receives the staple camming means, here provided in the form of an elongated drive rod 34 of the character shown in FIG. 2 having at its outboard end a finger engaging tab or pusher member 36.

With this construction drive rod 34 can be pushed longitudinally of slideway 38 by forces exerted on member 36. This forward movement of the drive rod causes sequential ejection of the staples 32 from the cartridge body 30 and, in the manner previously described, forces the staples into tissue disposed between jaw portions 12b and 14b of the structural members and into forming engagement with a disposable anvil member 70 (FIG. 1).

An extremely important aspect of the surgical stapler of this latest form of the invention is a novel jaw stabilizer means which is carried by the removable anvil portion of the instrument. As before, this jaw stabilizing means functions to restrict bending of the handle portions of the structural members as the tissue disposed between the jaw portions thereof is compressed as a result of the structural members moving toward the closed position shown in FIG. 16. This latest form of jaw stabilizing means, comprises a stabilizing member 72 which is connected proximate one end of an elongated spring segment 74, the other end of which is connected to removable anvil 70. Spring segment 74 includes a generally flat central portion 74a which is movable from a first position shown in FIG. 15 wherein it extends angularly with respect to disposable anvil 70 to a second position shown in FIG. 16 wherein it is generally aligned with the anvil. Disposable anvil 70 can be removably connected to jaw portion 12b in any suitable manner well known to those skilled in the art.

Figure 18:
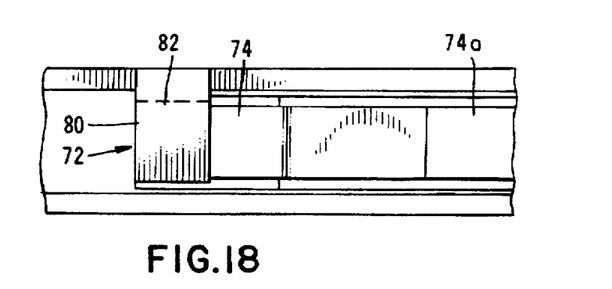
FIG. 18 is a view taken along lines 18—18 of FIG. 16.
Figure 18A:
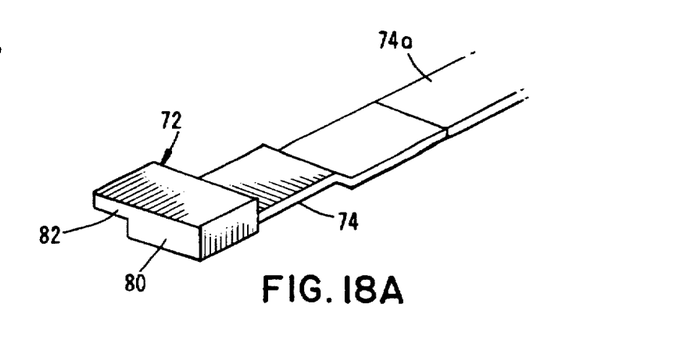
FIG. 18A is a generally perspective view of a portion of the stabilizer means of this latest form of the invention for restricting bending of the handle portions of the structural members of the instrument.

The stabilizer member of this latest form of the invention is somewhat similar to that shown in FIG. 14 and comprises a central body portion 80 from which a spacer segment 82 extends (FIGS. 18 and 18A). Segment 82 extends between handle portions 12a and 14a of the structural members (FIG. 17) and, as previously described, is controllably crushable.

As was the case with stabilizer member 57, member 72 is preferably molded in a single piece from a suitable type of moldable plastic having physical characteristics such that portion 82 of the stabilizer member will be controllably crushed to a predetermined extent as the structural members 12 and 14 move into their closed position due to the actuating of locking member 20.

Figure 19:
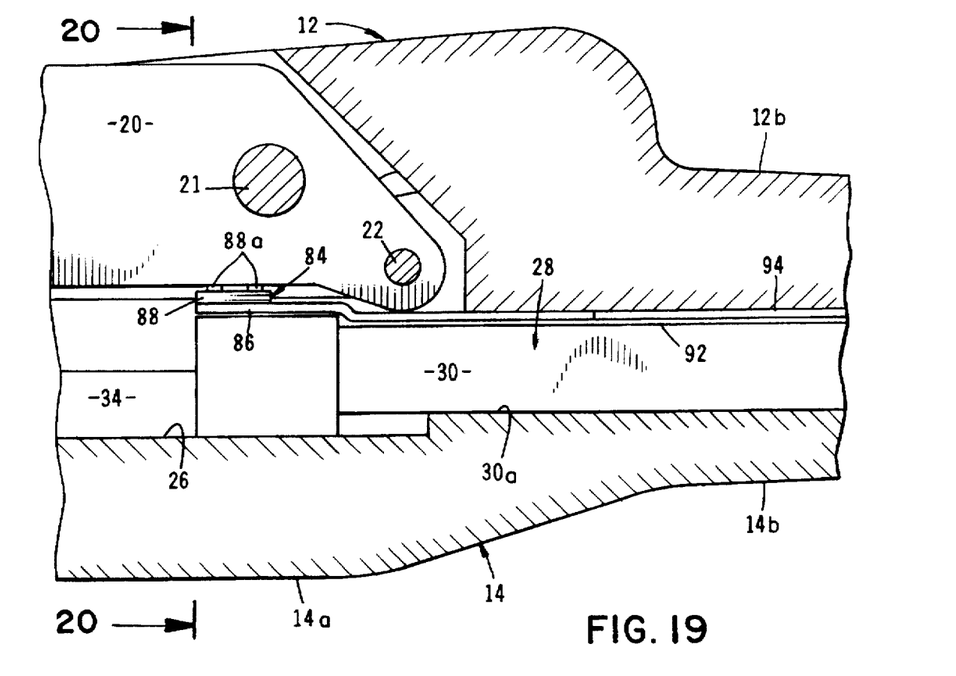
FIG. 19 is an enlarged, fragmentary, side-elevational view of the central portion of still another form of the improved surgical stapler of the invention.
Figure 20:
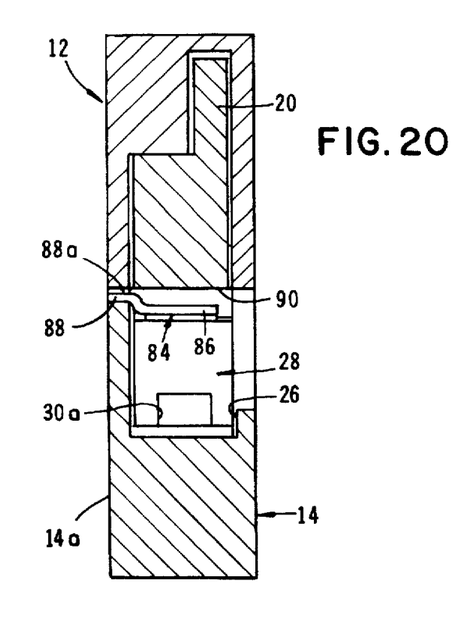
FIG. 20 is a cross-sectional view taken along lines 20—20 of FIG. 19.
Figure 21:
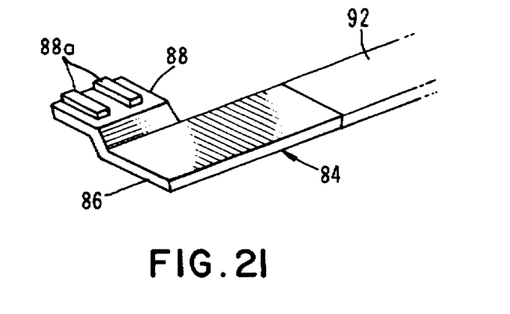
FIG. 21 is a generally perspective view of a portion of the stabilizer means of the form of the invention shown in FIGS. 19 and 20.

An alternate form of jaw stabilizing means of the invention is illustrated in FIGS. 19 and 21. This alternate form of stabilizing means is somewhat similar to that shown in FIGS. 5 through 10 and comprises a stabilizer member 84 having central body portion 86 from which a spacer segment 88 extends in one direction. Spacer segment 88 extends between handle portions 12a and 14a of the structural members and into the space 90 which is defined thereby when the handle portions are in their closed position (FIGS. 19, 20 and 21A). Like the crushable jaw stabilizer means, this latest form of stabilizer means, or member 84, is connected proximate one end of an elongated spring segment 92, the opposite end of which is connected to a removable anvil portion 94. Spacer segment 88 is provided with upstanding protuberances 88a (FIG. 21A) which are of a precisely determined thickness that effectively restricts bending and deflection of the handle portions 12a and 14a of the instrument in response to separating forces applied to the jaw portions by the tissue being compressed therebetween.

As previously mentioned, since a new anvil assembly is provided after each stapling operating, a new stabilizer means is also presented each time the instrument is used for the stapling procedure. This elegantly solves the problem inherent in devices of the character described in the '088 patent since, even if some slight deformation to spacer segment 88 occurs during the stapling operation, a fresh spacer element is provided for the next ensuing stapling operation.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A surgical stapler comprising:
   (a) first and second structural members each having:
      (i) a handle portion having first and second ends;
      (ii) a jaw portion having first and second ends; and
      (iii) pivot means located proximate said second ends of said handle portions for free engagement and disengagement, said pivot means, when engaged, permitting pivotal movement of said structural members between a closed position wherein said jaw portions are in a closely spaced relationship to an open position wherein said jaw portions are spaced further apart;
   (b) a locking member having first and second ends, said locking member being pivotally connected to said first structural member for pivotal movement relative thereto between a first position wherein said locking member is generally aligned with said first structural member and a second position wherein said second end of said locking member is spaced apart from said second end of said first structural member, said locking member being engageable with said second structural member and functioning upon movement from said second position toward said first position to forcefully move said first and second structural members toward said closed position;
   (c) stapling means, including a staple cartridge carrying a plurality of staples, removably connected to one of said first and second structural members, for stapling together tissue disposed between said jaw portions of said structural members as said structural members are moved into said closed position;
   (d) anvil means connected to the other of said first and second structural members for forming said staples carried by said staple cartridge; and
   (e) jaw stabilizer means for restricting bending of said handle portions of said structural members as the tissue disposed between said jaw portions thereof is compressed as a result of said structural members moving toward said closed position, said jaw stabilizer means being connected to one of said stapling means and said anvil means and comprising a spacer segment being disposed intermediate said handle portions of said structural members as said structural members move toward said closed position.

2. A surgical stapler as defined in claim 1 in which said spacer segment comprises a rigid element.

3. A surgical stapler as defined in claim 1 in which said spacer segment comprises a crushable element.

4. A surgical stapler comprising:
   (a) first and second structural members each having:
      (i) a handle portion having first and second ends;
      (ii) a jaw portion having first and second ends; and
      (iii) pivot means located proximate said second ends of said handle portions for free engagement and disengagement, said pivot means, when engaged, permitting pivotal movement of said structural members between a closed position wherein said jaw portions are in a closely spaced relationship to an open position wherein said jaw portions are spaced further apart;

(b) a locking member having first and second ends, said locking member being pivotally connected to said first structural member for pivotal movement relative thereto between a first position wherein said locking member is generally aligned with said first structural member and a second position wherein said second end of said locking member is spaced apart from said second end of said first structural member, said locking member being engageable with said second structural member and functioning upon movement from said second position toward said first position to forcefully move said first and second structural members toward said closed position;

(c) stapling means, including a staple cartridge carrying a plurality of staples, removably connected to one of said first and second structural members, for stapling together tissue disposed between said jaw portions of said structural members as said structural members are moved into said closed position, said staple cartridge comprising a central sleeve portion having a groove;

(d) anvil means connected to the other of said first and second structural members for forming said staples carried by said staple cartridge; and (e) jaw stabilizer means for restricting bending of said handle portions of said structural members as the tissue disposed between said jaw portions thereof is compressed as a result of said structural members moving toward said closed position, said jaw stabilizer means being connected to one of said stapling means and said anvil means and comprising a stabilizing member connected to said staple cartridge, said stabilizer member having a spacer segment extending between said handle portions of said structural members as said structural members move toward said closed position, said stabilizing member further including a tongue portion receivable within said groove of said central sleeve portion of said stable cartridge, said spacer segment being connected to and extending from said tongue portion.

* * * * *